United States Patent
Kondo et al.

(12) 
(10) Patent No.: US 6,316,691 B1
(45) Date of Patent: Nov. 13, 2001

(54) ATRICHIA MOUSE

(75) Inventors: Taizo Kondo; Toshio Kondo, both of Naruto; Yasuhisa Shiomoto, Tokushima, all of (JP)

(73) Assignee: Otsuka Pharmaceutical Factory, Inc., Tokushima (JP)

( * ) Notice: Subject to any disclaimer, the term of this patent is extended or adjusted under 35 U.S.C. 154(b) by 0 days.

(21) Appl. No.: 09/230,735

(22) PCT Filed: Jul. 30, 1997

(86) PCT No.: PCT/JP97/02661

§ 371 Date: Feb. 3, 1999

§ 102(e) Date: Feb. 3, 1999

(87) PCT Pub. No.: WO98/05202

PCT Pub. Date: Feb. 12, 1998

(30) Foreign Application Priority Data

Aug. 5, 1996 (JP) .................................... 8-223093

(51) Int. Cl.⁷ ........................ A01K 67/00; A01K 67/027
(52) U.S. Cl. ....................... 800/9; 800/8; 800/11
(58) Field of Search .................... 800/8, 9, 11; 514/326, 514/861, 864

(56) References Cited

FOREIGN PATENT DOCUMENTS

WO90/06367 6/1990 (WO).

OTHER PUBLICATIONS

Gilhar, A. et al. Hair Growth in Human Split Thickness Skin Grafts Transplanted onto Nude Rats: The Role of Ciclosporin. Dermatologica 181:117–121, 1990.*

Gilhar, A. et al. Topical Cyclosporin Induces Hair Growth in Human Split Skin Grafted Onto Nude Mice, Acta Derm. Venereol. 71:327–330, 1991.*

Moore, G.J. Dermatitis in Nude Mice (nu/nu) Associated with *Staphylococcus pyogenes*. Laboratory Animals 17:42–44, 1983.*

Murakami, R. et al. The Effect of Azelastine on Acute Radiation Dermatitis in Mice Models. International Journal of Radiation Oncology Biology Physics 37(4):907–911, 1997.*

Kondo et al, *Mouse Genome,* 95:698–700 (1997).

Kligman, *Clinics in Dermatology,* 6(4):163–168 (1988).

Rothnagel et al, *J. of Invest. Dermatology,* US, New York, NY. 102(4):547 (1994).

Palm et al, *The Journal of Heredity,* 67:284–288 (1976).

* cited by examiner

*Primary Examiner*—Deborah J. R. Clark
*Assistant Examiner*—Janet M Kerr
(74) *Attorney, Agent, or Firm*—Sughrue, Mion, Zinn, Macpeak & Seas, PLLC

(57) ABSTRACT

The invention relates to an atrichia mouse which grows juvenile hair but is deficient in the ability to grow pelage hair and, more particularly, to an atrichia mouse such that the spontaneous prevalence of wet and dry skin lesions is not less than 70%. at the 24th week of age, the number of mast cells in the skin is not less than about 50/linear mm at the 24th week of age, and the serum IgE level is not less than about 3500 ng/ml at the 24th week of age. The atrichia mouse of the invention finds application as an animal model of disease for the research and development of therapeutic drugs for dermatitis, among other kinds of drugs.

5 Claims, 13 Drawing Sheets

F I G. 1 6
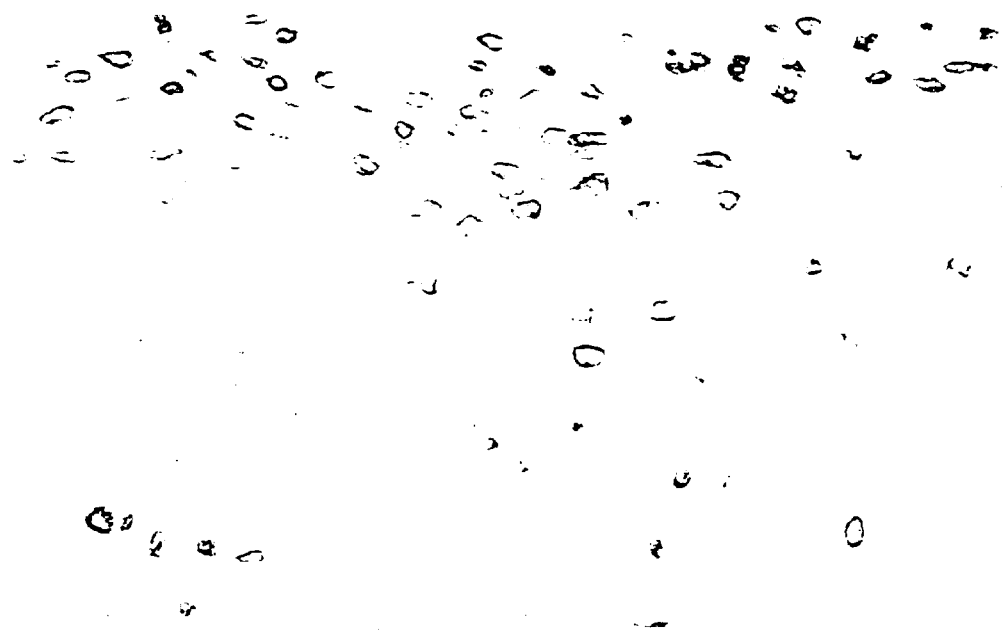

ATRICHIA MOUSE

TECHNICAL FIELD

The present invention relates to an atrichia mouse and more particularly to a novel atrichia mouse capable of growing juvenile hair but deficient in the ability to grow pelage hair.

BACKGROUND ART

As the animals in routine use in studies on therapeutic drugs for dermatitis, among other diseases, the mouse, rat, and rabbit can be mentioned. However, there is the disadvantage that in order that those animals may be actually used in such studies, they must be subjected to various pretreatments. In a screening for antiallergic drugs, for instance, animals which have undergone PCA (passive cutaneous anaphylaxis) reaction are used as is well known. However, to induce this PCA reaction in animals, an antiserum containing a homologous or heterologous tissue reagin must be administered to denuded animals and for quantification of this reaction, an antigen and a dye or radiolabeled albumin must be administered intravenously after a certain interval of time (48–168 hours when the homologous PCA IgE antibody was used). (Hiroichi Nagai: 2-1 Dermatitis (1) PCA Reaction, Seibutsu-Yaku-Kagaku Jikken Koza (Biopharmaceutical Science Experiment Series) Vol. 12, Inflammation and Allergy (I-1) (ed. Kazuo Ohuchi), Hirokawa Shoten, Tokyo, 1993, p.96–109). The foregoing means not only the absolute need for such pretreatment procedures but also the risk for the experimenter being exposed to the antiserum and other factors which might adversely affect his or her health. Therefore, development of an animal model of disease, which might be submitted to studies on therapeutic drugs, such as drugs for dermatitis, without said or other pretreatments, has been awaited.

The object of the present invention, therefore, is to provide an animal model of disease meeting the above demand.

During, intensive investigations, the inventors succeeded in producing an atrichia mouse suited for the object. The present invention is based on the above results.

DISCLOSURE OF THE INVENTION

The present invention relates to an atrichia mouse comprising having the ability to grow juvenile hair but being deficient in the ability to grow pelage hair and more particularly to such an atrichia mouse showing a 70% or higher spontaneous prevalence of wet (ulcerative) and dry skin lesions at and after the 24th week of age, such an atrichia mouse in which the number of mast cells in the skin is not less than about 50 cells/linear mm at the 24th week of age, and such an atrichia mouse in which the serum immunoglobin E (IgE) level is not less than about 3500 ng/ml at the 24th week of age.

As mentioned above, the atrichia mouse of the invention is characterized by the ability to grow juvenile hair but the inability to grow pelage hair. Mice with such a deficiency in pelage hair-growing ability have not been established, or even reported, to this day.

Furthermore, the atrichia mouse of the invention is characterized in that the spontaneous prevalence of wet and dry skin lesions is not less than 70% at and after the 24th week of age, that the number of mast cells in the skin is not less than about 50 cells/linear mm at the 24th week of age, and that the serum IgE level is not less than about 3500 ng/ml at the 24th week of age.

Meanwhile, the ordinary hair mouse does not spontaneously develop wet or dry skin lesions and its number of mast cells in the skin is usually about 10 cells/linear mm according to the data generated by the present inventors. With regard to the serum IgE level, it is usually very low although few quantitative determinations have been reported and no normal level has been postulated. Incidentally, according to the determination by the present inventors (using, the test kit described hereinafter), the IgE level was 0.0–137.5 ng/ml in ICR mice at the $16^{th}$ week of age and 0.0–5.0 ng,/ml in ddY mice at the $16^{th}$ week of age as shown hereinafter ill Tables 3 and 4. As reported in the literature, the IgE level in normal mice is <20–608 ng/ml in BALB/c mice and <20 ng/ml in all C3H mice and the level in animals experimentally infected with a parasite (*Nipopostronoylus brasiliensis*) is 2240–7168 ng/ml in BALB/c mice and 1365–3068 ng/ml in C3H mice (Takao Hirano & Hiroaki Miyajima: Characterizations and applications of rat monoclonal murine IgE antibody, Medical Immunology, 15(2), 211–216 (1988)).

Furthermore, even the existing hairless mice do not develop wet or dry skin lesions spontaneously and their number of mast cells in the skin calculated by the present inventors is generally about 20 cells/linear mm. With regard to the serum IgE level, the level found by the present inventors (using the test kit described hereinafter) was 102.0–253.0 ng/ml in HRS/J mice at the 20th week of age as shown hereinafter in Table 2.

In contrast, the atrichia mouse of the invention is characterized by an exceptionally high prevalence of spontaneous skin lesions, a high number of mast cells in the skin, and a high serum IgE level at (or after) the 24th week of age as mentioned above and, in those aspects, distinctly different from any of the ordinary hairy mouse and existing hairless mice, thus substantiating its novelty.

On the strength of the above characteristics, the atrichia mouse of the invention is of great use in the screening for prophylactic and therapeutic drugs for dermatitis and as an animal model of disease for experiments for efficacy evaluation and other purposes.

Furthermore, even prior to the $24^{th}$ week of age, the atrichia mouse of the invention presents a steady hairless condition as compared with the existing hairless mice and denuded mice and therefore, offers the advantage that individuals without development of skin lesions (particularly animals of low age) can be used without requiring the trouble of hair clipping as experimental animals for the dermal irritation study of drugs to be administered transdermally, inclusive of medicines and cosmetics.

The present invention, therefore, further provides a method of testing the efficacy and/or dermal irritation potential of drugs to be applied to the skin, such as medicinal and cosmetic preparations, typically prophylactic and therapeutic drugs for dermatitis, by using the above atrichia mouse of the invention.

The above-mentioned test according to the invention can be carried out in the same manner as the routine tests of the kind except that the use of the atrichia mouse of the invention is an essential requisite. For example, a typical test procedure comprises applying a test substance in a dosage form suited to transdermal administration, such as an ointment or a plaster, and in a suitable dose to the skin of the atrichia mouse of the invention in the conventional manner and monitoring with the passage of time of its action and effect in accordance with the ordinary observation and evaluation protocol.

The atrichia mouse of the invention is originated from a sparsely coated mutant (male) which was accidentally discovered in the process of brother-sister breeding, of the hybrid mice between a female C3H/He mouse and a male ddY mouse. When the above-mentioned sparsely coated mouse was subjected to brother-sister mating with a female mouse of the littermate, only male sparsely coated animals were obtained up to the subsequent second generation but male and female sparsely coated animals were obtained in the third generation. By subjecting those male and female sparsely coated animals to brother-sister mating, the female atrichia animal of the invention was obtained, and by subjecting this female atrichia animal to brother-sister mating with a male sparsely coated animal of the littermate, male and female atrichia animals could be obtained. Using those male and female atrichia animals as the atrichia $F_0$ on, they were subjected to brother-sister mating, whereupon all the offspring became atrichia animals. In this manner, the atrichia mouse of the invention was successfully fixed and established. The atrichia mouse of the invention will hereinafter be referred to as the Naruto Research Institute Otsuka Atrichia (hereinafter, "NOA") mouse.

The method of breeding mice of the above respective generations need not be particularly different from the method of breeding ordinary mice and may for example comprise breeding the animals in suitable cages with access to a suitable food under barrier-system conditions at a temperature of 23±2° C. and a relative humidity of 55±5%., with 12-hour lighting from 7:00 a.m. to 7:00 p.m. [cf. Shin Jikken Dobutsu Gaku, Asakura Shoten, p.104, 1986, for instance]. As the food mentioned above, a solid food (typically CRF-1, Oriental Yeast Industry Co., Ltd.) can be utilized. Tap water can be used for drinking, and allowing free access.

The situation of hair growth and the development of skin lesions during the above breeding period can be observed with the naked eye and the number of mast cells in the skin and the serum IgE level can be determined by the routine procedures, for example by the toluene blue staining of tissue specimens and the sandwich ELISA method using, a commercial mouse IgE test kit, respectively.

The thus-fixed atrichia mouse of the invention (the NOA mouse) is maintained by the present applicant in a constantly available condition and its embryos have been deposited with American Type Culture Collection, Park Lawn Drive 12301, Rockville, Md., USA 20852 (ATCC) under the accession number of 72022.

BRIEF DESCRIPTION OF THE DRAWINGS

FIG. 16 is a photograph in lieu of a drawing, which shows IgE staining test findings by immunohistology (biomorphology) of the skin (the dorsal skin with dry lesions) of a NOA mouse (48th week of age, male).

BEST MODE FOR CARRYING OUT THE INVENTION

The following examples are intended to illustrate the present invention in further detail.

EXAMPLE 1

A sparsely coated male mutant mouse obtained by cross breeding a female C3H/He mouse and a male ddY mouse, as origins, was subjected to brother-sister mating with a female animal of the littermate and the male and female sparsely coated animals of the third generation were further subjected to brother-sister mating to obtain a female atrichia animal. This female atrichia animal was subjected to brother-sister mating with a male sparsely coated animal of the littermate to obtain a male and a female atrichia animal. Then, these male and female atrichia animals, as the $F_0$ generation, were subjected to brother-sister mating to fix the atrichia mouse line of the present invention (the NOA mouse).

The breeding of the respective mice was performed using breeding cages (bottom size: 170×280 mm×H130 mm, polycarbonate, CLEA Japan, Inc.) by the group breeding method using a maximum of 5 animals/cage. The breeding was carried out under barrier-system conditions (temperature 23±2° C., relative humidity 55±5%, a 12-hour lighting cycle of 7.00 a.m. to 7.00 p.m.) allowing free access to solid food (CRF-1, Oriental Yeast Industry, Co., Ltd.) and tap water for drinking.

The NOA mice obtained as above were observed for the following parameters.

Parameter 1: Situation of hair loss—by macroscopic observation. With regard to Rhino mice, however, the evaluation was made in accordance with the method described in the literature [A. Howard, "Rhino", an allele of hairless in house mouse, J. Hered., 31, 467–470 (1940); Stanley, J. Mann, Hair loss and cyst formation in Hairless and Rhino mutant mice., ANAT. REC., 170, 485–500 (1971); Kawaji, H., Tsukuda, R. and Nakaguchi, T., Immunopathology of Rhino mouse, An autosomal recessive mutant with murine lupus-like disease., Acta Pathol, Jpn., 30 (4), 515–530 (1980)].

Parameter 2: Spontaneous development of skin lesions—by macroscopic observation.

Parameter 3: Number of mast cells in the skin—by staining tissue specimens with toluidine blue.

Parameter 4: IgE—production

1. Staining of IgE—by the immunohistology (ABC method).
2. Serum IgE level by the sandwich ELISA method.

The results obtained are described below.

Parameter 1: Situation of Hair Loss

The NOA mice of the invention and, as comparative animals, HRS/J and BALB/cA-hr hairless mice were respectively observed macroscopical over a period from the 5th to the 48th week of age. However, the Rhino mice were observed and evaluated in accordance with the above literature.

(1) NOA Mice

Figure 1:
FIG. 1 is a photograph in lieu of a drawing, which shows the external appearance of a NOA mouse (5th week of age, male).
Figure 2:
FIG. 2 is a photograph in lieu of a drawing, which shows the external appearance of a NOA mouse (10th week of age, male).

These animals grow juvenile hair but are deficient in the ability to grow pelage hair, and the body hair disappears by the 10th week of age when juvenile hair are lost. Moreover, the vibrissae in the nasorostral and palpebral region are short, deformed, and irregular (5th week of age; FIG. 1). Thereafter at around the 12th week of age, the vibrissae in the nasorostral and palpebral region are also lost and the entire body becomes completely hairless and smooth-skinned (10th week of age; FIG. 2).

(2) HRS/J Mice

Figure 3:
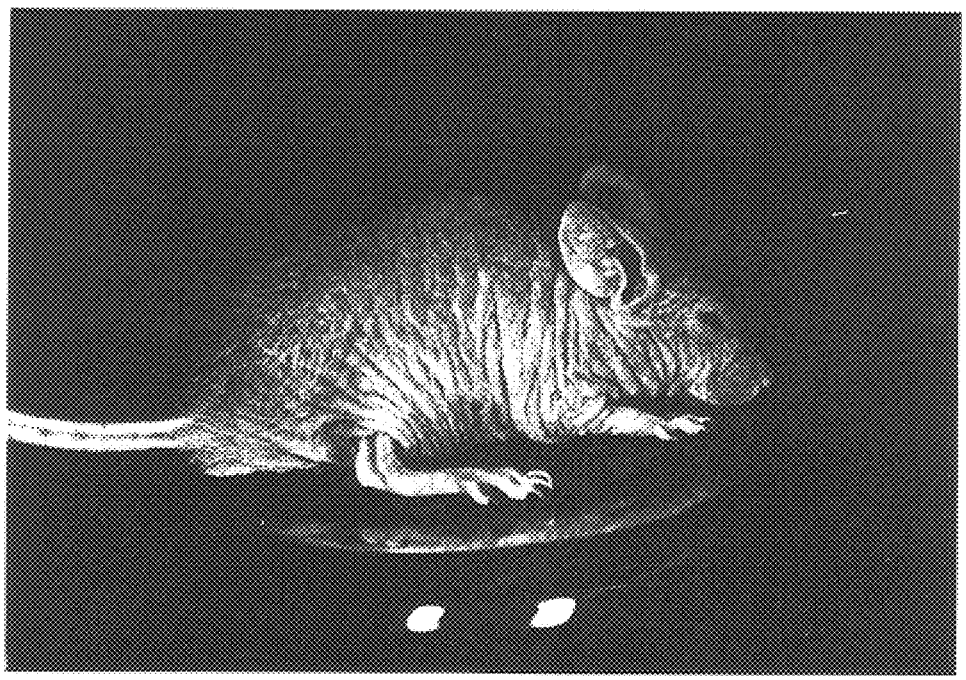
FIG. 3 is a photograph in lieu of a drawing, which shows the external appearance of a comparative HRS/J mouse (7th week of age, male).
Figure 4:
FIG. 4 is a photograph in lieu of a drawing, which shows the external appearance of a comparative HRS/J mouse (28th week of age, male).

In addition to the ability to grow juvenile hair, the ability to grow pelage hair is still retained, so that pelage hair, though sparse, is observed (7th week of age; FIG. 3). As the animals continue to grow, this pelage hair is lost and a hairless skin appears (28th week of age; FIG. 4) but the body hair is still observed in same animals as late as the 20th week of age, thus a marked individual difference being found. The skin after the hair loss is more deeply wrinkled as compared with the NOA mouse.

The vibrissae in the nasorostral and palpebral region are normal (28th week of age; FIG. 4).

(3) BALB/cA-hr Mice

Figure 5:
FIG. 5 is a photograph in lieu of a drawing, which shows the external appearance of a comparative BALB/cA-hr mouse (7th week of age, male).
Figure 6:
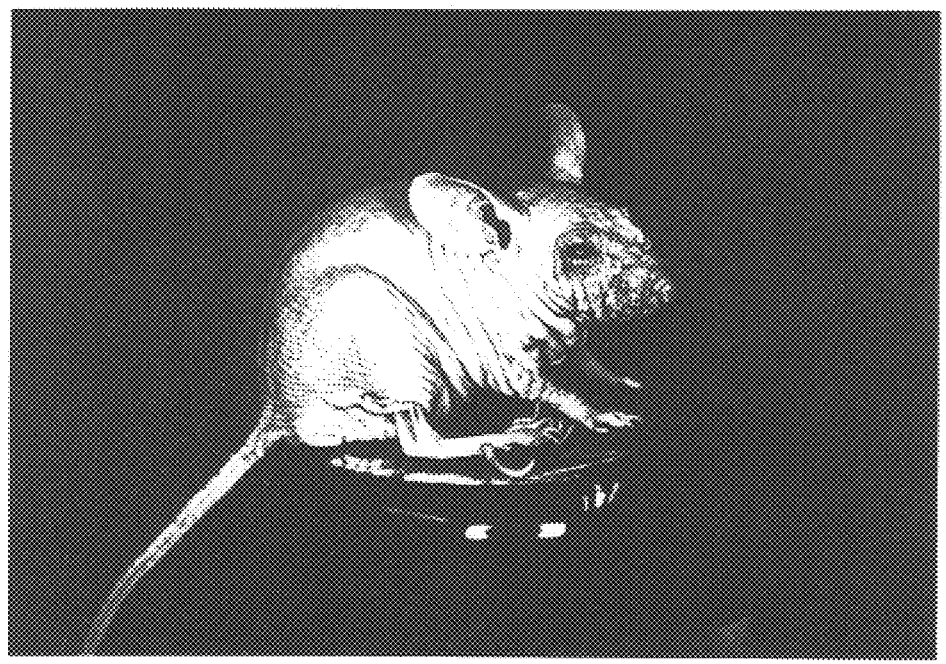
FIG. 6 is a photograph in lieu of a drawing, which shows the external appearance of a comparative BALB/cA-hr mouse (28th week of age, male).

Findings in those mice are almost similar to those in HRS/J mice. Thus, in addition to the ability to grow juvenile hair, the ability to grow pelage hair is still retained, and some pelage hair, though sparse, is observed (7th week of age; FIG. 5). As the animals continue to grow, this pelage hair is lost and a hairless skin appears. (28th week of age; FIG. 6) but the body hair is still observed in some animals as late as the 20th week of age. Thus, individual difference is noted. The skin after the hair loss is more wrinkled as compared with the NOA mouse, showing a roughness.

The vibrissae in the nasorostral and palpebral region are normal (28th week of age; FIG. 6).

(4) Rhino Mice

The exterior features are normal until the 13th to 14th week of age but hair loss begins in the region above the eyes and continued to expand until the 3rd to 4th week of age, with the result that the hair remains only on the limbs, tail, and ears. The sparsely hair remains on the back until the 5th week of age and the hair on the hind limbs remains until the 7th week of age [A. Howard, "Rhino", an allele of hairless in house mouse, J. Hered., 31, 467–470 (1940)].

The following description is found in Stanley, J. Mann, Hair loss and Cyst Formation in Hairless and Rhino Mutant Mice, ANAT. REC., 17, 485–500 (1971). The mutant mice grew a first hair coat and appear identical to their non-mutant littermates until about 12 days after birth. At this time, loss of hair begins around the eyes in the mutant Genotypes and subsequent loss of hair proceeds in a caudal direction. By 25 days of age, hrhr mutant skin is devoid of all general body hair but $hr^{rh}hr^{rh}$ mutant skin retains a few scattered hairs until about 60 days of age. The above descriptions suggest that, in Rhino mice, in addition to the ability to grow juvenile hair, the ability to row pelage hair is still retained.

The above report of A. Howard mentions also that while vibrissae remain through life, senescence make them short and crooked and many of them shed off. On the other hand, the following literature mentions that the vibrissae in the nasorostral and palpebral region are normal (Kawaji, H.,Tsukuda, R. and Nakaguchi. T., Immunopathology of Rhino mouse, An autosomal recessive mutant with murine lupus-like disease., Acta Pathol. Jpn., 30 (4), 515–530 (1980)).

Parameter 2: Spontaneous Development of Skin Lesions

The NOA mice of the invention and, as comparative animals, HRS/J and BALB/cA-hr of hairless mouse were respectively observed with the naked eye over a period from the 5th to the 48th week of age.

(1) NOA Mice

The spontaneous development of skin lesions began around the 10th week of age. While both dry (dry skin) and wet (ulcerative skin) lesions are observed, they are not different lesions, the only difference being whether the epidermis remains or not.

The skin lesions initially appear as flare which then progresses to dry or wet lesions. The progression to wet lesions appears to result from the ease of shedding of the epidermis which leads to spontaneous exfoliation or exfoliation due to a physical stimulus. The lesions in which the epidermis does not shed off but remains is regarded as dry skin lesions but many dry lesions appear to develop into wet lesions with time.

With regard to wet skin lesions, most of them are minute at low ages and it is not earlier than around the 16th week of age that extensive lesions are found. It is after the 24th week of age that still more extensive wet lesions are found at a high prevalence.

Figure 7:
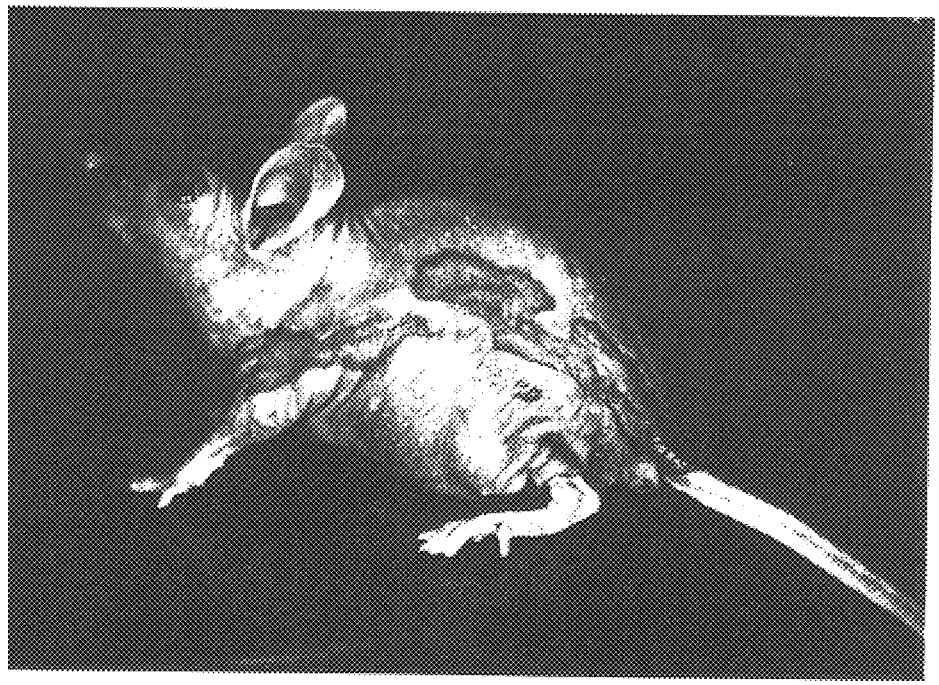
FIG. 7 is a photograph in lieu of a drawing, which shows the external appearance of a NOA mouse (20th week of age, male) development with wet skin lesions.
Figure 8:
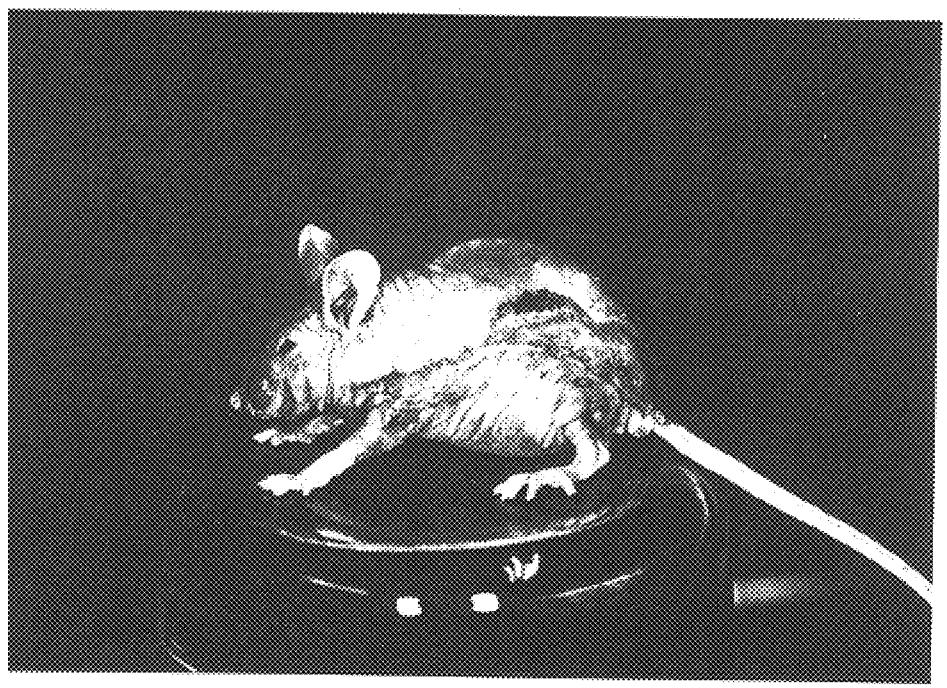
FIG. 8 is a photograph in lieu of a drawing, which shows the external appearance of the NOA mouse shown in FIG. 7 after 4 weeks.
Figure 9:
FIG. 9 is a photograph in lieu of a drawing, which shows the external appearance of the NOA mouse shown in FIG. 7 after 12 weeks.
Figure 10:
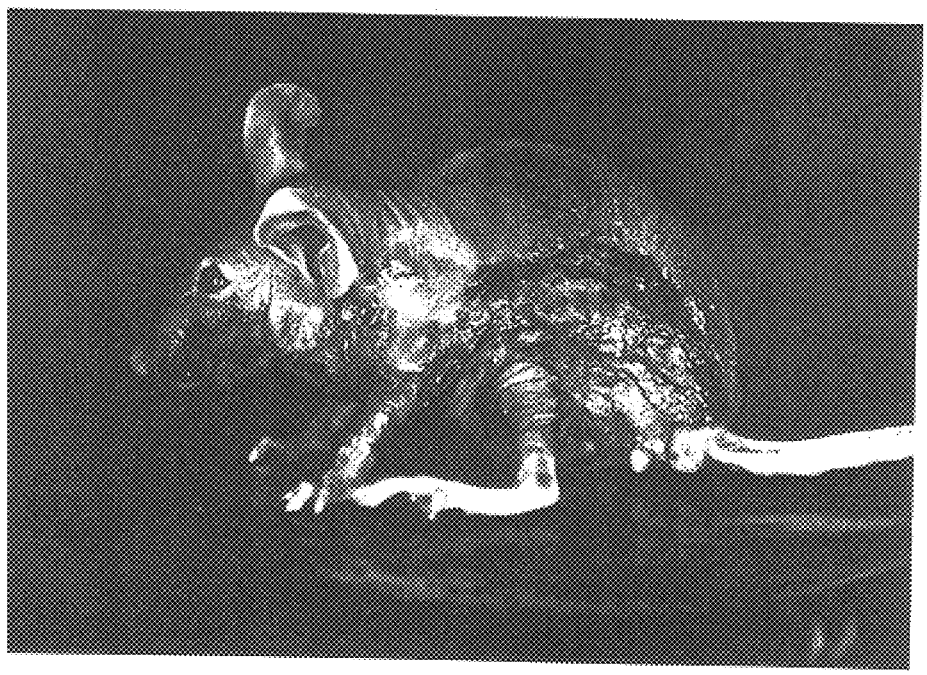
FIG. 10 is a photograph in lieu of a drawing, which shows the external appearance of the NOA mouse shown in FIG. 7 after 16 weeks.

The passage of time of gradual expansion of wet skin lesions with aging is as shown in FIGS. 7 to 10. FIG. 7 represents a NOA mouse at the 20th week of age and FIG. 8 represents the same NOA mouse 4 weeks later (24th week of age). FIG. 9 represents the same mouse after a further 12 weeks (36th week of age) and FIG. 10 represents the same mouse after a further 16 weeks (40th week of age).

The respective figures are now explained in detail. In FIG. 7 (20th week of age), wet skin lesions are observed in the left palpebral superior through nasorostral region and the shoulder-back-lumbar region. In the back-lumbar regions, dry skin lesions accompanied by a small amount of desquamation and evidence of a roughness are observed.

In FIG. 8 (24th week of age), expansion of wet skin lesions is observed (a tendency toward improvement is observed locally in the palpebral superior through nasorostral region). In the area presenting with dry skin lesions, epidermal fragility and thinning is observed.

In FIG. 9 (36th week of age), a further expansion of affected area is observed in the wet skin lesion (local improvement in the palpebral superior through nasorostral region) and a progression of skin fragility and thinning is found in the dry skin lesion.

In FIG. 10 (40th week of age), a further expansion is observed in the wet skin lesion and a further progression of skin fragility and thinning is found in the dry skin lesion.

Among severe cases of the above skin lesions, those in which the affected area accounts for more than 20% of the body surface are observed. Wet skin lesions may undergo remission in some cases but in no case has been observed a complete remission of extensive lesions.

Dry skin lesions are found as a roughness at low ages but a higher degree of desquamation and a marked fragility and thinning of the epidermis is observed at advanced ages.

Figure 11:
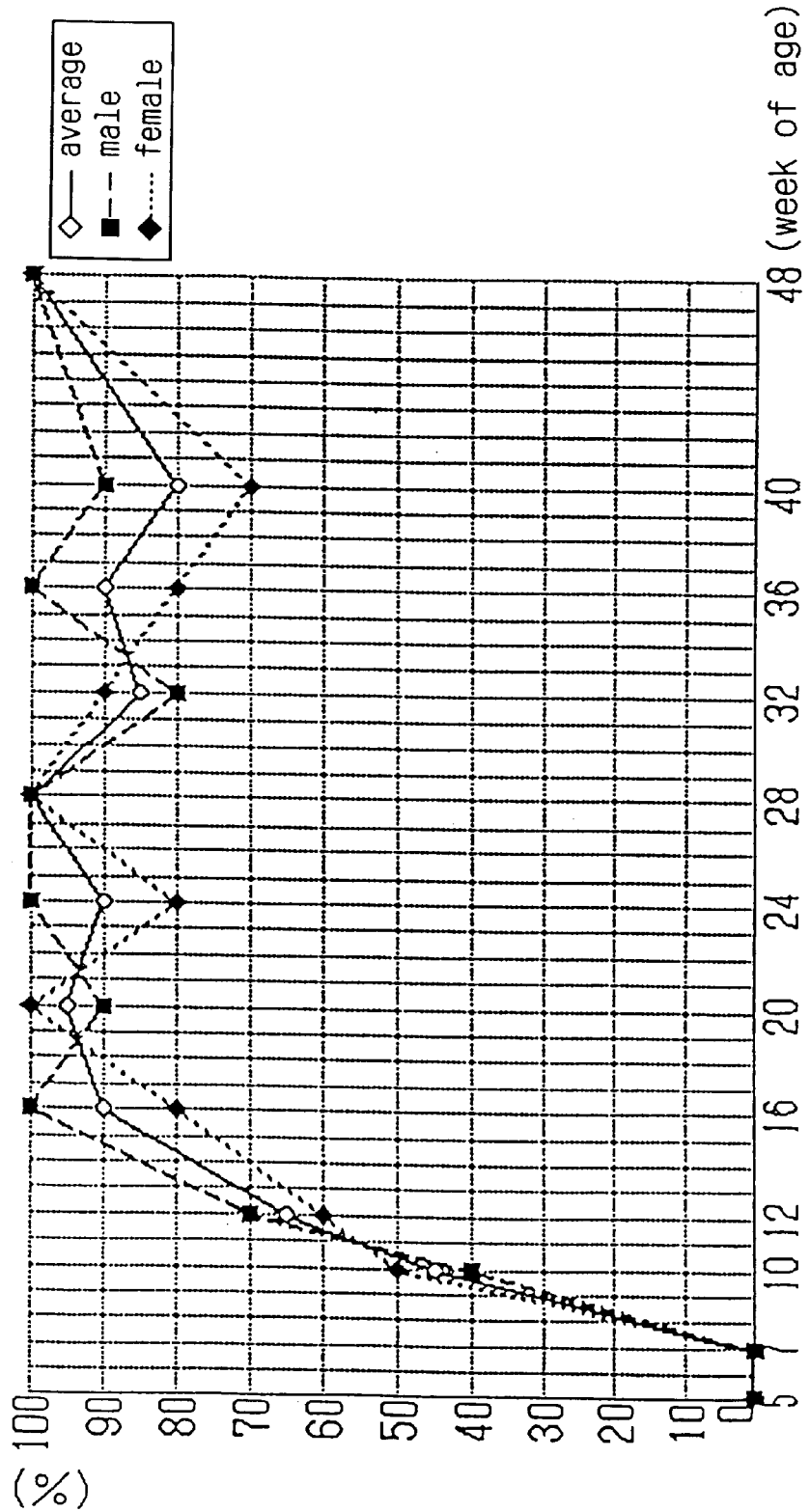
FIG. 11 is a diagrammatic representation of the total prevalence of skin lesions, wet and dry lesions combined, in NOA mice (male and female), by week of age.

The prevalence of the above skin lesions is shown in FIG. 11.

FIG. 11 is a diagrammatic representation of the total prevalence of skin lesions, dry and wet, in 10 NOA mice of either sex at each week of age.

With regard to the prevalence of skin lesions, the animals presenting with grossly definite skin lesions by macroscopic observation were regarded as affected cases.

In the figure, the "average" means the average of male and female cases, "n" is 10 of either sex at each week of age, the number of examination weeks of age is 12, and the total number of animals examined is 120 for either sex (total 240).

It is obvious from FIG. 11 that the prevalence of skin lesions, both dry and wet, is as high as 90% on the average of two sexes at the 16th week of age.

Figure 12:
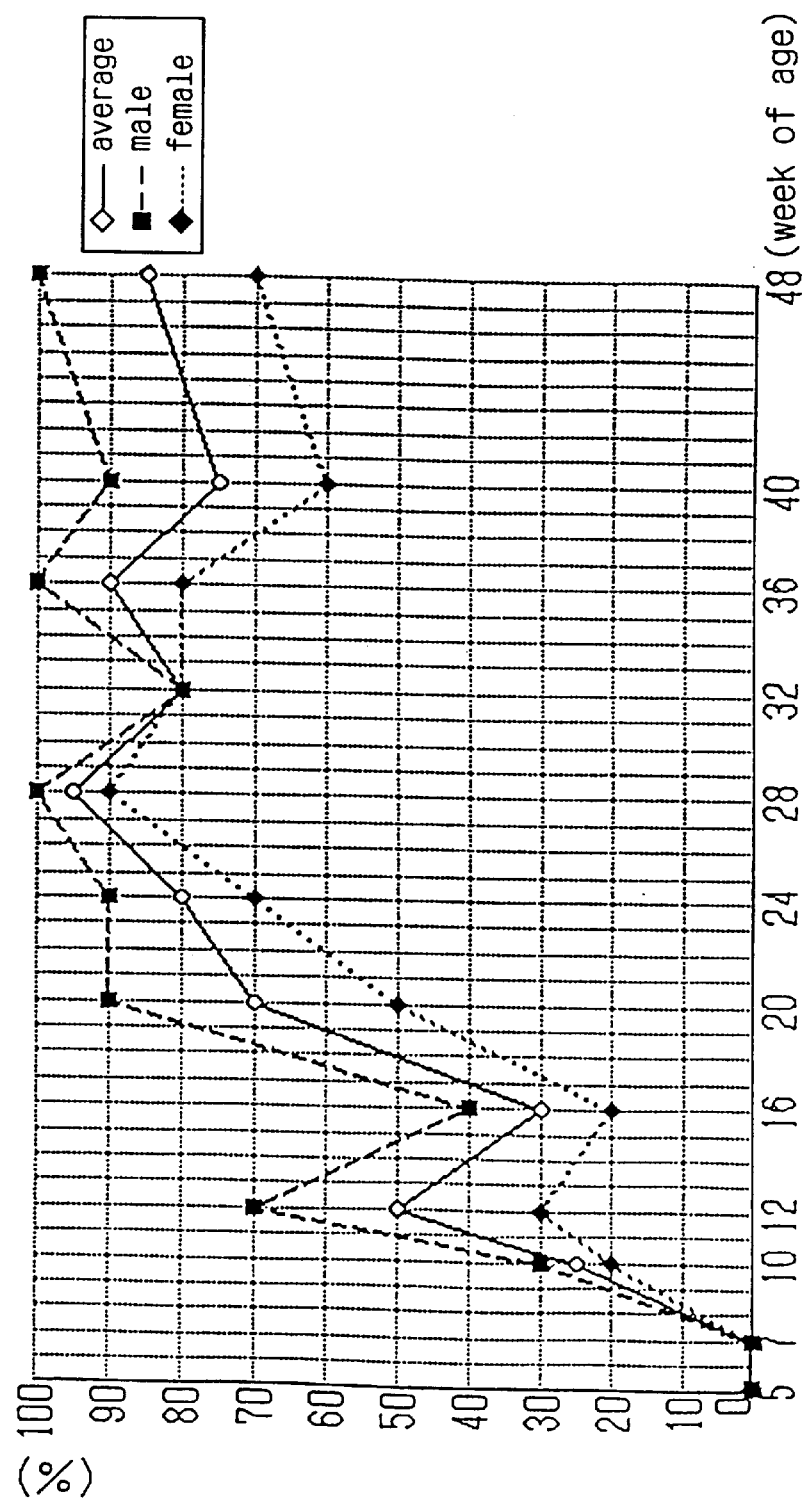
FIG. 12 is a diagrammatic representation of the prevalence of wet skin lesions only as determined in the same manner as for FIG. 11.

FIG. 12 shows the prevalence of wet skin lesions only as similarly determined.

It is clear from FIG. 12 that the average prevalence of wet skin lesions in male and female animals is 30% at the 16th week of age and as high as 80% at the 24th week of age.

(2) HRS/J Mice and BALB/cA-hr Mice

Throughout the breeding period (the 5th to 48th week of age), minute wet lesions (trauma) apparently attributable to fighting were observed in several cases but, even in those animals, no expansion of the lesions ensued but the lesions became remissive and disappeared in about 2 weeks.

Parameter 3: Number of Mast Cells in the Skin

In the histopathological examination of NOA mice, large number of mast cells were found in the skin lesion. This finding suggested the proliferation of mast cells in the skin of NOA mice. To verify the finding, the number of mast cells in the skin was determined as follows.

Thus, from the skin in the back, lumbar region, chest, and abdominal region, approximately 1-centimeter-long samples were respectively prepared and stained with toluidine blue, and the mast cells per linear millimeter were counted in 3 positions (right and left ends and center) under the light-microscope. The counts were averaged to arrive at the mean numbers of mast cells in the back, lumbar region, chest, and abdominal region, respectively. In addition, the mean numbers in those 4 regions were averaged to arrive at the number of mast cells in the skin of the particular animal.

As controls, similar experiments were performed using HRS/J and BALB/cA-hr of hairless mice as comparative animals and, ICR and ddY of ordinary hairy mice as controls animals.

Figure 13:
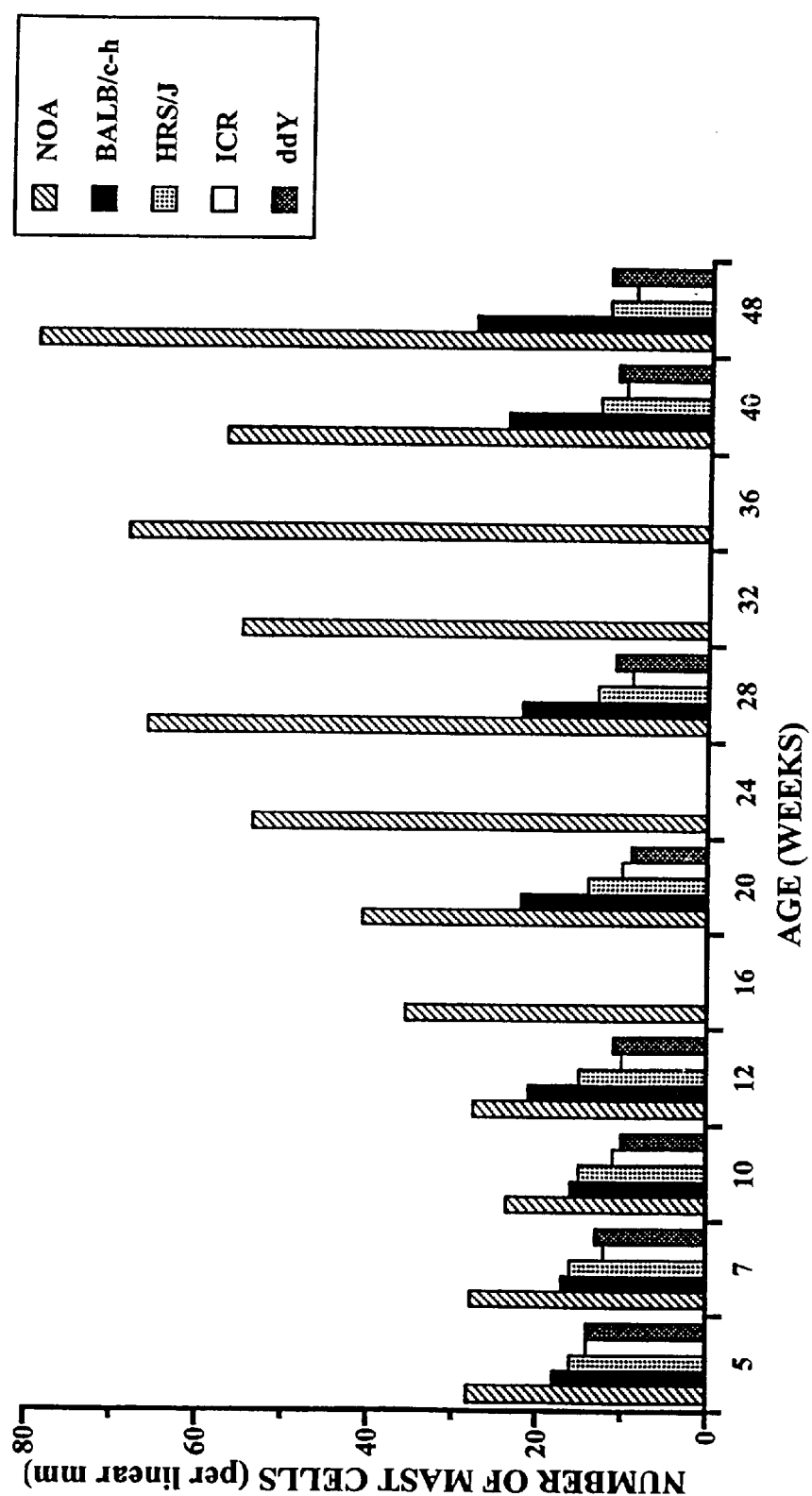
FIG. 13 is a diagrammatic representation of the time course of the number of mast cells in the skin in NOA mice in comparison with the comparative and control mice.

The results are presented in FIG. 13 [ordinate: number of mast cells/mm; abscissa: age (in weeks) of mouse].

The number of mice of each strain (n; all males) was 10 for the NOA mouse at each week of age (12 examination weeks; total number of animals examined: 120) and 5 per strain for comparative or control animals at each week of age (8 examination weeks; total number of animals examined: 30 per strain). The NOA mice were randomly sampled without regard to the presence or absence of skin lesions. The data on HRS/J mice are indicated by the legend HRS/J, the data on BALB/cA-hr mice by the legend BALB/C-h, the data on ICR mice by the legend ICR, and the data on ddY mice by the legend ddY.

It can be seen from FIG. 13 that the number of mast cells in the skin in the NOA mice of the invention was 28/linear mm at the 12th week of age and 57/linear mm at the 40th week of age. These values are definitely higher than the corresponding values in the comparative and control animals. In fact, the numbers of mast cells in HRS/J mice were 15/linear mm at the 12th week of age and 13/linear mm at the 40th week of age, those in BALB/cA-hr mice were 21/linear mm at the 12th week of age and 24/linear mm at the 40th week of age, those in ICR mice were 10/linear mm at the 12th week of age and 10/linear mm at the 40th week of age, and those in ddY mice were 11/linear mm at the 12th week of age and 11/linear mm at the 40th week of age.

Figure 14:
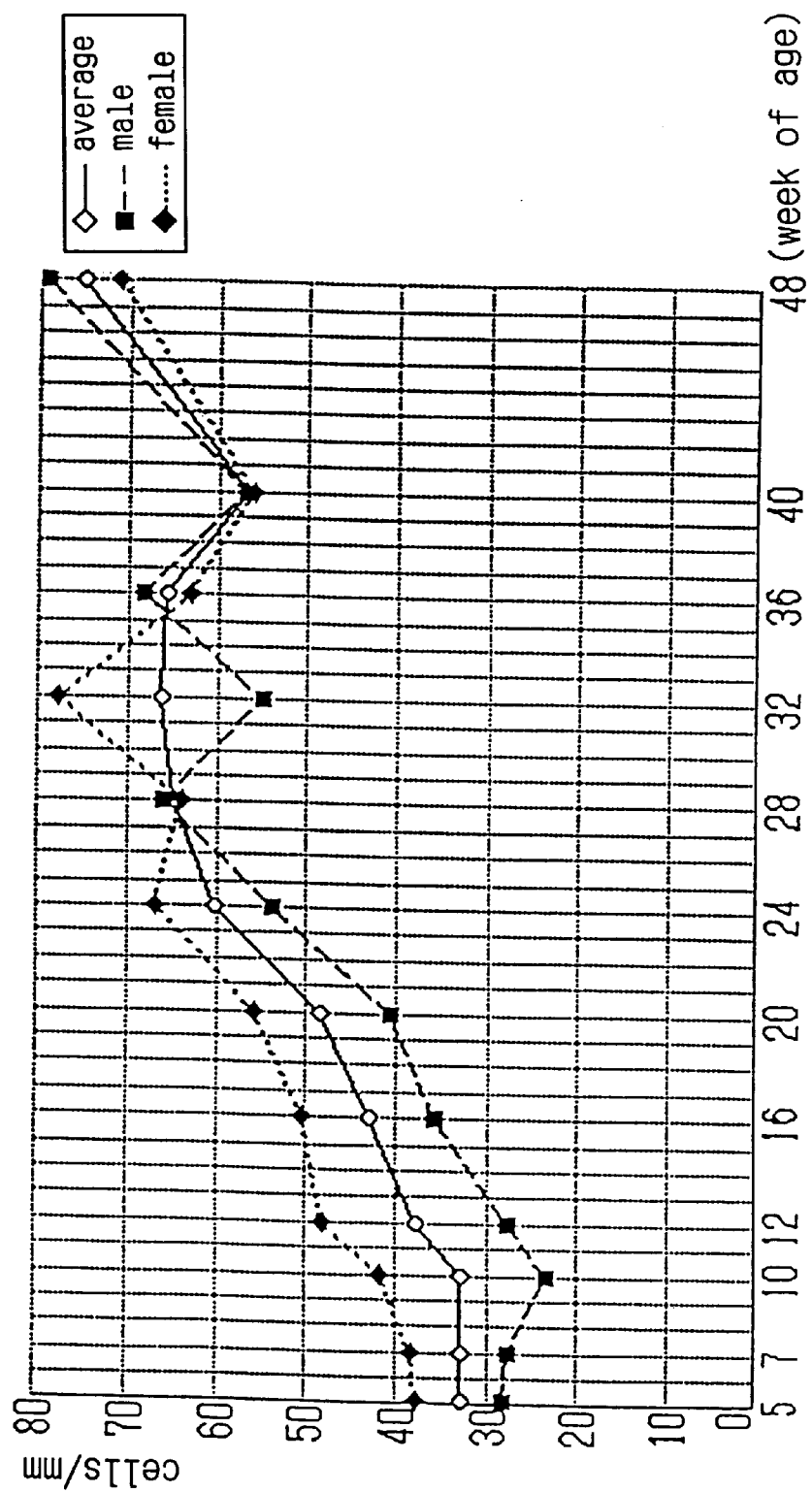
FIG. 14 is a diagrammatic representation of the time course of the number of mast cells in the skin in NOA mice (male and female).

Furthermore, in NOA mice, some sex-dependent difference was noted in the number of mast cells. This can be seen from FIG. 14 which was plotted in the same manner (using the same number of animals) as FIG. 11.

Furthermore, in NOA mice, the number of mast cells in the skin depended on the condition of the skin. Thus, compared with the intact skin area, the number of mast cells was larger in the affected skin area (FIG. 15; where the "mean" represents the average number of mast cells calculated without regard to the presence or absence of skin lesions, "wet" represents a wet skin lesion and "dry" represents a dry skin lesion, and "normal" represents an intact skin area). In some cases, significantly high values were found in the lesion and adjoining area, with local counts even in excess of 300 cells/linear mm being observed.

Figure 15:
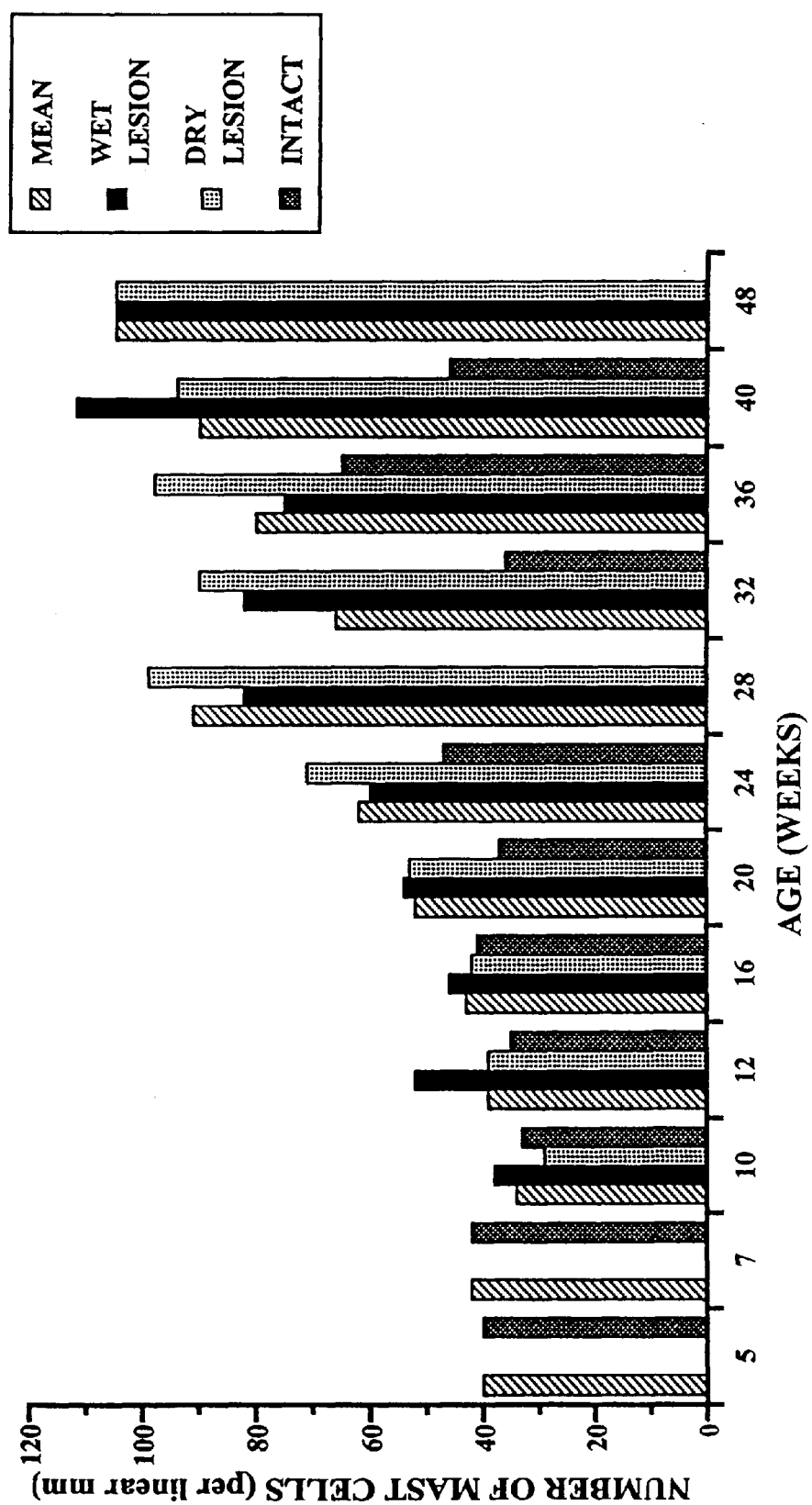
FIG. 15 is a diagrammatic representation of the time course of the number of mast cells in each of the skin area with wet lesions, skin area with dry lesions, and intact area of the dorsal skin of a NOA mouse (male).

The number of animals examined (n) in FIG. 15 is 10 for each week of age, the number of examination weeks is 12, the total number of animals examined is 120, and the number of animals (n) corresponding to each parameter (condition) is as follows:

5th week of age: wet skin lesion=0, dry skin lesion=0, intact skin=10

7th week of age: wet skin lesion=0, dry skin lesion=0, intact skin=10

10th week of age: wet skin lesion=3, dry skin lesion=1, intact skin=6

12th week of age: wet skin lesion=2, dry skin lesion=2, intact skin=6

16th week of age: wet skin lesion=3, dry skin lesion=1, intact skin=6

20th week of age: wet skin lesion=4, dry skin lesion=5, intact skin=1

24th week of age: wet skin lesion=4, dry skin lesion=4, intact skin=2

28th week of age: wet skin lesion=5, dry skin lesion=5, intact skin=0

32nd week of age: wet skin lesion=3, dry skin lesion=3, intact skin=4

36th week of age: wet skin lesion=5, dry skin lesion =3, intact skin=2

40th week of age: wet skin lesion=3, dry skin lesion=5, intact skin=2

48th week of age: wet skin lesion=6, dry skin lesion=4, intact skin=0.

The above results clearly indicate a marked proliferation of mast cells in the skin in NOA mice and suggest that this mast cell proliferation is related to the development of skin lesions.

Parameter 4: IgE antibody production (1) IgE Staining Findings by Immunohistology From NOA mice, HRS/J and BALB/cA-hr of hairless mice as comparative animals, and ICR and ddY of hairy mice as control animals, the skin, body surf ace lymph nodes, thymus, and spleen were respectively isolated, and the IgE antibodies were stained by the enzyme-antibody method (ABC method) and observed under the light-microscope.

The test mice were under observation throughout the period from the 5th to 48th week of age.

As a result, in NOA mice, an intense positive reaction was found around the mast cells in the skin and many positive cells (suspected to be IgE producing plasma cells) were observed in the body surface lymph nodes beginning around the 12th week of age. This reaction was comparatively more intense in animals with skin lesions, and showed a greater number of positive cells in those animals. Furthermore, in some of the animals with skin lesions, a positive reaction (suspected to be deposition of IgE complexes) was found in the dendritic reticulum cells in the germinal center of the lymph node. Those findings can be seen in FIG. 16 (NOA mouse, 48th week of age, dry skin lesion in the dorsal skin), FIG. 17 (NOA mouse, 24th week of age, mandibular lymph node in an animal with wet skin lesions), and FIG. 18 (NOA mouse, 32nd week of age, germinal center of the mandibular lymph node in an animal with wet skin lesions). Each figure is a microphotograph (magnification×150) of each site and the same applies to FIG. 19 (dorsal skin) and FIG. 20 (mandibular lymph node).

Referring to FIG. 16, the ring-like or punctate stain (black) represents an IgE positive cell and, here, all such stains represent mast cells.

Figure 17:
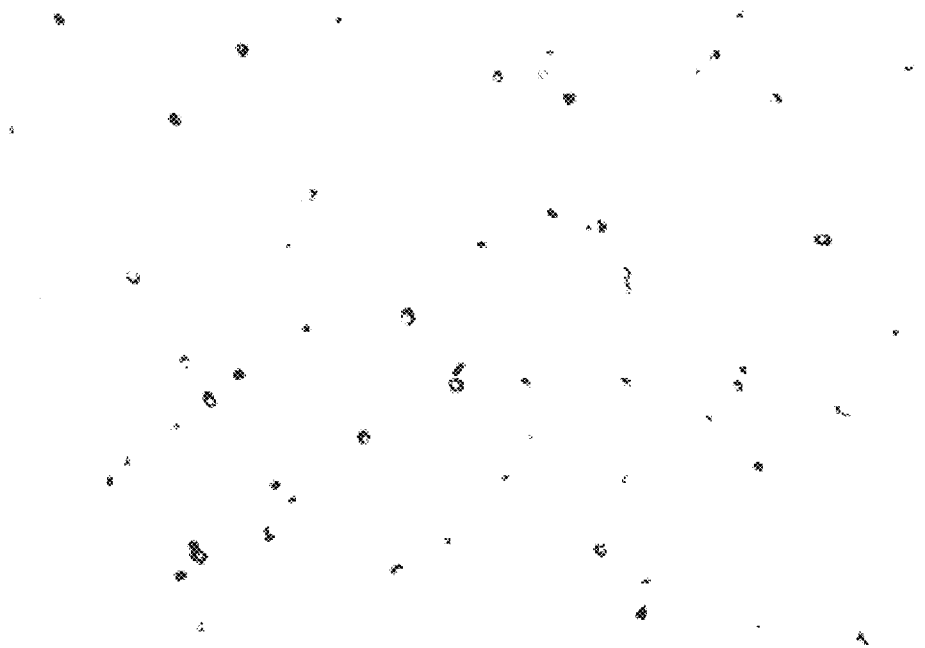
FIG. 17 is a photograph in lieu of a drawing, which shows IgE staining test findings by immunohistology of the body surf ace lympho node (mandibular lymph node) of a NOA mouse (24th week of age, male).

Referring to FIG. 17, the dot-like stain (black) represents an IgE positive cell and, here, all such stains are considered to be IgE producing plasma cells.

Figure 18:
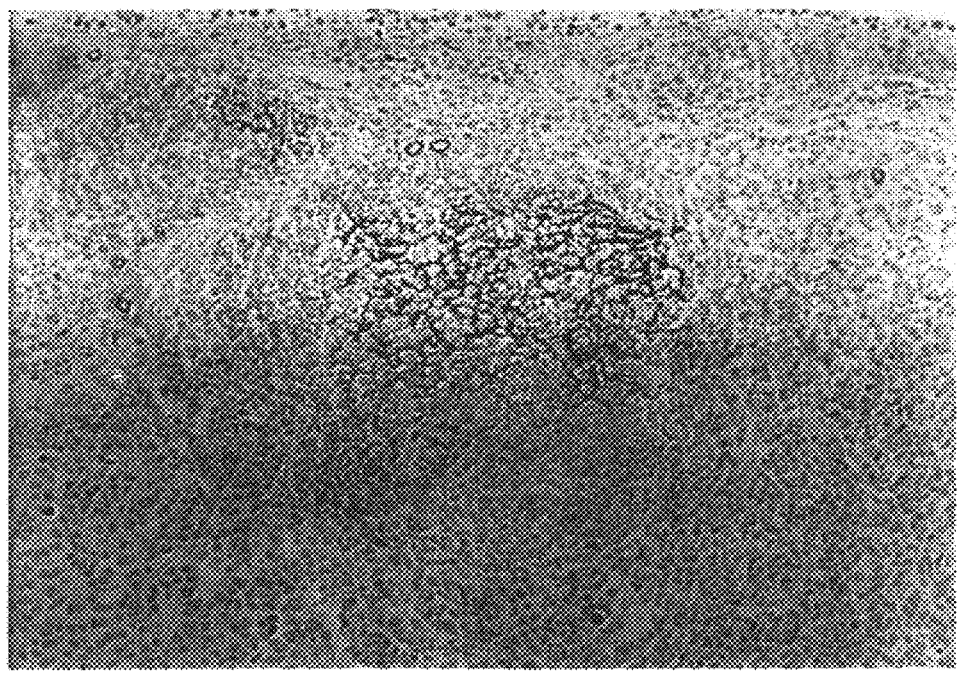
FIG. 18 is a photograph in lieu of a drawing, which shows IgE staining test findings by immunohistology of the germinal center of the body surf ace lymph node (mandibular lymph node) in a NOA mouse (32nd week of age, male).

Referring to FIG. 18, the mesh-like stain (black) in the center indicates a positive reaction and, here, it is considered to be the deposition of IgE complexes on the dendritic reticulum cells in the germinal center.

Figure 19:
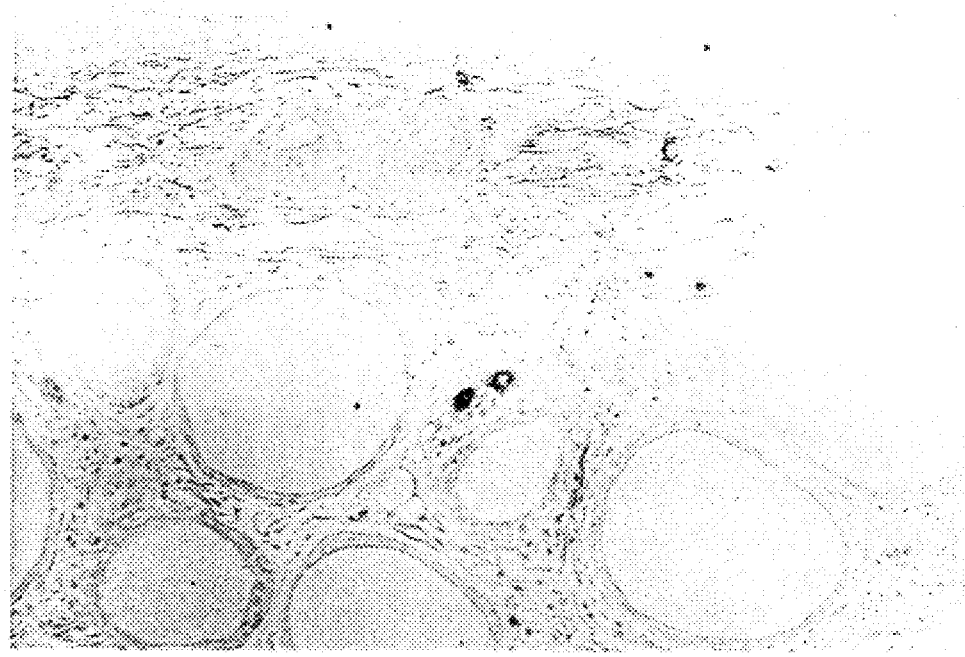
FIG. 19 is a photograph in lieu of a drawing, which shows IgE staining test findings by immunohistology of the skin (back) of a comparative BALB/cA-hr mouse (20th week of age, male).
Figure 20:
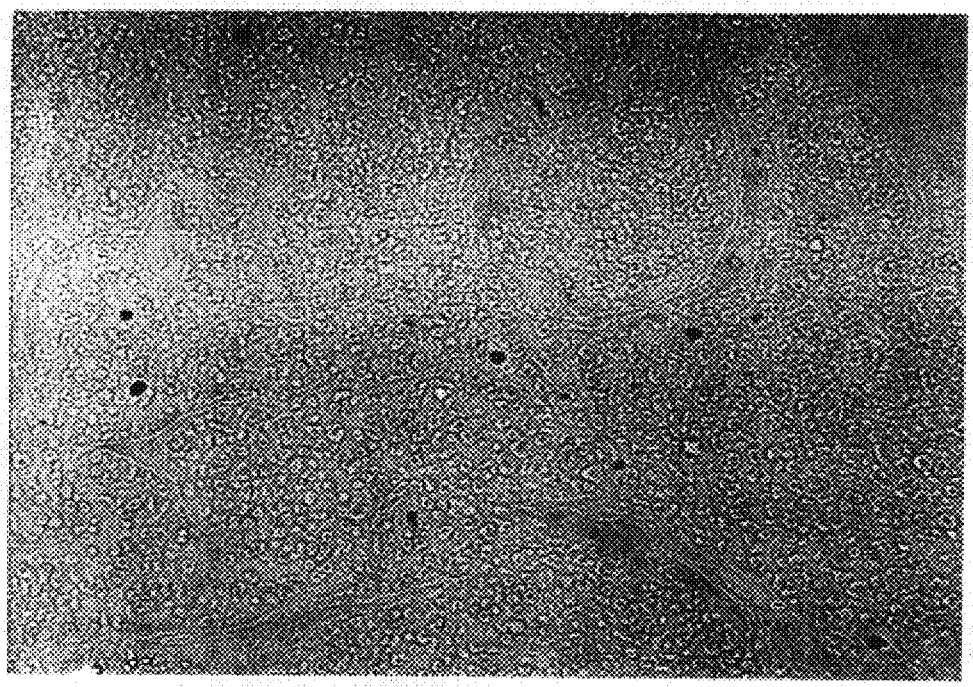
FIG. 20 is a photograph in lieu of a drawing, which shows IgE staining test findings by immunohistology of the body surface lymph node (mandibular lymph node) in a comparative BALB/cA-hr mouse (28th week of age, male).

This is in contrast with the pictures in comparative animals. Thus, as can be seen in FIGS. 19 and 20, all are weak reactions or only a few positive cells are observed. FIG. 19 is a microphotograph of the back skin of a BALB/cA-hr mouse at the 20th week of age and FIG. 20 is a microphotograph of the mandibular lymph node of a BALB/cA-hr mouse at the 28th week of age.

Referring to FIG. 19, the several cells each stained in a ring-like (black) are IgE positive cells which, here, are mast cells.

Referring to FIG. 20, the several cells each stained in a dot-like (black) are positive cells which, here, are considered to be IgE producing plasma cells.

The above results clearly indicate an increased production of IgE in the NOA mouse and suggest that this increased IgE production is related to the development of skin lesions.

(2) Determination of the Serum IgE Level

While the above staining findings (1) suggested an increased production of IgE in the NOA mouse, the following quantitative determination of serum IgE level was carried out to endorse the above findings.

Thus, using a commercial test kit (tradename: MOUSE IgE EIA KIT YAMASA, Yamasa Shoyu Co., Ltd. ), the serum IgE level was measured by the sandwich ELISA method.

The results obtained for NOA mice (male, the 5th to 32nd week of age) are presented below in Table 1. Referring to the table, the severity rating scale for lesions is as follows. The symbol "−" represents an animal without skin lesions and the symbols "+" through "+++" represent animals with wet skin lesions in an increasing order of affected area from "+" to "+++". The symbol "W" means that the animal has developed dry skin lesions.

As controls, the serum IgE level was similarly determined in HRS/J mice (male, 5th, 20th, and 28th weeks of age), ICR mice (male, 5th, 16th, and 32nd weeks of age) , and ddY mice (male, 5th, 16th, and 32nd weeks of age). The results are presented below in Tables 2, 3, and 4.

TABLE 1

| | (NOA mice) | | |
|---|---|---|---|
| Week of age | Animal No. | Severity of lesion | Serum IgE level (ng/ml) |
| 5th week | 1 | − | 126.3 |
| | 2 | − | 176.1 |
| | 3 | − | 130.9 |
| | 4 | − | 117.0 |

TABLE 1-continued (NOA mice)

| Week of age | Animal No. | Severity of lesion | Serum IgE level (ng/ml) |
|---|---|---|---|
| 10th week | 1 | – | 112.4 |
|  | 2 | – | 523.7 |
|  | 3 | – | 198.1 |
|  | 4 | – | 191.8 |
|  | 5 | W | 182.4 |
|  | 6 | + | 151.4 |
|  | 7 | + | 280.4 |
|  | 8 | + | 130.9 |
| 16th week | 1 | W | 431.9 |
|  | 2 | W | 188.6 |
|  | 3 | W | 807.5 |
|  | 4 | + | 1023.9 |
|  | 5 | ++ | 5586.3 |
|  | 6 | ++ | 2878.8 |
|  | 7 | ++ | 2071.7 |
| 24th week | 1 | + | 3877.3 |
|  | 2 | + | 4907.1 |
|  | 3 | +++ | 7676.2 |
|  | 4 | +++ | 15527.9 |
|  | 5 | +++ | 16212.6 |
| 32nd week | 1 | + | 1787.8 |
|  | 2 | ++ | 16424.3 |
|  | 3 | ++ | 23742.4 |
|  | 4 | +++ | 7902.6 |
|  | 5 | +++ | 17756.5 |

TABLE 2

(HRS/J mice)

| Week of age | Animal No. | Severity of lesion | Serum IgE level (ng/ml) |
|---|---|---|---|
| 10th week | 1 | – | 102.0 |
|  | 2 | – | 112.0 |
|  | 3 | – | 130.0 |
|  | 4 | – | 140.0 |
|  | 5 | – | 151.0 |
| 20th week | 1 | – | 102.0 |
|  | 2 | – | 125.0 |
|  | 3 | – | 165.0 |
|  | 4 | – | 194.0 |
|  | 5 | – | 253.0 |
| 28th week | 1 | – | 100.0 |
|  | 2 | – | 128.0 |
|  | 3 | – | 140.0 |
|  | 4 | – | 184.0 |
|  | 5 | – | 186.0 |

TABLE 3

(ICR mice)

| Week of age | Animal No. | Severity of lesion | Serum IgE level (ng/ml) |
|---|---|---|---|
| 5th week | 1 | – | 7.5 |
|  | 2 | – | 75.0 |
|  | 3 | – | 75.0 |
| 16th week | 1 | – | 0.0 |
|  | 2 | – | 25.0 |
|  | 3 | – | 137.5 |
| 32nd week | 1 | – | 150.0 |
|  | 2 | – | 215.0 |
|  | 3 | – | 290.0 |

TABLE 4

(ddY mice)

| Week of age | Animal No. | Severity of lesion | Serum IgE level (ng/ml) |
|---|---|---|---|
| 5th week | 1 | – | 0.0 |
|  | 2 | – | 0.0 |
|  | 3 | – | 0.0 |
| 16th week | 1 | – | 0.0 |
|  | 2 | – | 0.0 |
|  | 3 | – | 5.0 |
| 32nd week | 1 | – | 0.0 |
|  | 2 | – | 0.0 |
|  | 3 | – | 27.5 |

Comparison of the above Tables 1 through 4 indicates clearly that compared with HRS/J, ICR, and ddY mice, the NOA mice show a considerably higher serum IgE level suggesting an increased production of IgE and suggests that this increased antibody production is related to the development of skin lesions.

What is claimed is:

1. A NOA atrichia mouse, which has matured from an embryo, saodd embryo having all of the identifying characteristics of embryos deposited with the American Type Culture Collection, deposit number ATCC 72022.

2. NOA atrichia mice which have matured from embryos having all of the identifying characteristics of embryos deposited with the American Type Culture Collection, deposit number ATCC 72022, and wherein a spontaneous prevalence rate of said mice with wet and dry skin lesions is not less than 70% of all of said mice at 24 weeks of age and thereafter.

3. The NOA atrichia mouse according to claim 1, wherein the mouse has a mast cell population in the skin of not less than about 50 cells/linear mm at the $24^{th}$ week of age.

4. The NOA atrichia mouse according to claim 1, wherein the mouse has a serum IgE level of not less than about 3500 ng/ml at the $24^{th}$ week of age.

5. The NOA atrichia mouse of claim 1, wherein the mouse grows juvenile hair, but does not grow pelage hair.

* * * * *